United States Patent [19]

Malbrancq et al.

[11] Patent Number: 4,687,580
[45] Date of Patent: Aug. 18, 1987

[54] MEMBRANE APPARATUS/PROCESS ADAPTED FOR PLASMAPHERESIS

[75] Inventors: Jean-Michel Malbrancq, Thiais; Elisabeth Bouveret, Paris; René Angleraud, Feyzin, all of France

[73] Assignee: Rhone-Poulenc S.A., Courbevoie, France

[21] Appl. No.: 456,821

[22] Filed: Jan. 10, 1983

[30] Foreign Application Priority Data

Jan. 11, 1982 [FR] France ................. 82 00485

[51] Int. Cl.⁴ ................................. B01D 13/00
[52] U.S. Cl. ................ 210/651; 210/195.2; 210/433.2; 210/927; 604/6
[58] Field of Search ............ 210/651, 257.2, 195.2, 210/433.2, 927, 411, 86; 604/6

[56] References Cited

U.S. PATENT DOCUMENTS

| 4,191,182 | 3/1980 | Popovich et al. | 210/433.2 X |
| 4,343,705 | 8/1982 | Legg | 210/195.2 X |
| 4,372,846 | 2/1983 | Yamagami et al. | 210/86 |
| 4,397,747 | 8/1983 | Ikeda | 210/86 X |
| 4,401,566 | 8/1983 | Igari et al. | 210/927 X |
| 4,411,792 | 10/1983 | Babb | 210/411 X |

FOREIGN PATENT DOCUMENTS

| 2100209 | 5/1972 | Fed. Rep. of Germany | 210/433.2 |
| 2745041 | 4/1978 | Fed. Rep. of Germany | 210/433.2 |
| 2939213 | 5/1980 | Fed. Rep. of Germany | 210/321.1 |
| 3043682 | 7/1981 | Fed. Rep. of Germany | 210/321.1 |
| 2198759 | 4/1974 | France | |
| 2457694 | 1/1981 | France | 210/651 |
| 79/00358 | 12/1979 | PCT Int'l Appl. | 210/651 |
| 81/00334 | 10/1981 | PCT Int'l Appl. | 210/651 |

Primary Examiner—Frank Spear
Attorney, Agent, or Firm—Burns, Doane, Swecker & Mathis

[57] ABSTRACT

Apparatus/process for the withdrawal and return of liquid materials from a donor source, comprising means for withdrawing whole blood from a mammalian donor; a membranous blood filtration cell which includes a membrane separator/filter, a compartment downstream therefrom for receiving a blood plasma fraction and a compartment upstream thereof for receiving a blood cellular component fraction; conduit means for communicating the withdrawal means and an inlet end of the upstream compartment; a collection vessel; conduit means for communicating an outlet end of said upstream compartment and said collection vessel; means for determining the volume of liquid material withdrawn from the donor source during a withdrawal stage; means for back-filtering and returning liquid material from said collection vessel to the donor source; a second collection vessel; and conduit means for communicating an outlet end of the downstream compartment and the second collection vessel.

37 Claims, 2 Drawing Figures

MEMBRANE APPARATUS/PROCESS ADAPTED FOR PLASMAPHERESIS

BACKGROUND OF THE INVENTION

1. Field of the Invention

The present invention relates to apparatus and process for plasmapheresis, and, more especially, to such apparatus/process employing a membrane separator.

2. Description of the Prior Art

Plasmapheresis is a known operation consisting of separating the whole blood of a donor into two fractions, the first fraction constituting the plasma phase and the second fraction constituting the cellular component phase, which is typically injected back into the donor. The plasma phase is a complex aqueous solution containing proteins in particular, while the cellular component phase, which still contains plasma, comprises the red corpuscles (or erythrocytes), the white corpuscles (or leucocytes) and the platelets.

The technique of plasmapheresis has long been used in animal experiments. Compare, for example, the article by John J. Abel et al entitled "Plasma Removal With Return Of Corpuscles" published at *J. Pharmacol. Exp. Ther.*, No. 5, pages 625 to 641 (1914), in which dog's blood is centrifuged in order to perform the separation. There may also be mentioned the article by A. Geiger published in *J. Phys.*, 71, pages 111–120 (1931) and entitled "Method Of Ultrafiltration In Vivo", which describes a continuous plasmapheresis operation on dogs, the separating apparatus employed being a membrane separator, and the membrane being arranged in a spiral and being selected such that it is possible, if desired, to obtain a plasmatic solution comprising the entirety of the proteins from the blood treated.

Plasmapheresis has also been applied to man for a certain number of years, as indicated by the article "La plasmapherese—Technique—Indications" ("Plasmapheresis—Technique—Indications") by Fr. Oberling et al, published at *J. Med. Strasbourg*, pages 277–279 (March, 1968). Thus, plasmapheresis now tends to replace the total donation of blood, because this technique has the advantage of enabling larger amounts of plasma to be withdrawn from a human donor without serious drawbacks. Because the formed elements of the blood are returned to the donor, the withdrawal sessions can be carried out at shorter intervals of time than for the donation of blood.

Thus, plasmapheresis is an old technique and the subsequent improvements which have been made thereto involve either improved centrifugation apparatus or improved membrane apparatus therefor. In the patent literature featuring improvements in membrane apparatus, reference is made to Amicon's German Patent No. 2,100,209 which describes a vessel comprising a membrane forming a spiral, for the circulation of whole blood withdrawn from a donor, and in which a pressure is exerted on the blood contained in the vessel, either by means of a gas or by means of the piston of a syringe, subjected to the action of a leaf spring. Compared with the apparatus of Geiger described above, this apparatus, by its very design, has the disadvantage of not permitting a continuous operation to be performed on the donor.

Also representative is Hemotherapy's U.S. Pat. No. 4,191,182 which describes membrane apparatus and in which blood continuously withdrawn from the donor is separated into plasma and into a cellular fraction continuously returned to the donor, such apparatus having the particular characteristic of allowing a portion of the cellular fraction to recirculate in the upstream compartment of the membrane apparatus and of allowing the plasma fraction to recirculate in the downstream compartment of the same apparatus. Cf. the International Application of Friedman et al published under International Publication No. WO 79/01121, which also deals with apparatus enabling the withdrawal of blood from the donor and injection back into the donor of the fraction which has not passed through the membrane, in a continuous operation.

However, the types of equipment described above, which permit continuous plasmapheresis, display the particular disadvantage of requiring the donor to be injected at two separate points, which is rather unpleasant for the donor.

SUMMARY OF THE INVENTION

Accordingly, a major object of the present invention is the provision of improved apparatus/process employing a membranous seperator which is well adapted for plasmapheresis operations on a donor, while entailing injecting the subject at but a single point with a blood withdrawal needle.

Another object of the present invention is the provision of improved plasmapheresis apparatus/process enabling subjecting the blood from the donor to a first separation by passage of same over a filtration membrane, and then to a second separation over the same membrane, as it is returned to the donor.

Another object of this invention is specially designed plasmapheresis apparatus enabling obtainment of plasma of very good quality and under the best conditions of filtration efficency, while at the same time guaranteeing virtually zero haemolysis of the blood.

Yet another object of this invention is the provision of improved plasmapheresis apparatus enabling the user to regulate the pressure at which the cellular component fraction exits the upstream compartment of the membrane apparatus to relative pressure values which are typically between 0 and 20 mm of mercury, the downstream compartment being at atmospheric pressure.

Still another object of this invention is the provision of plasmapheresis apparatus making it possible to withdraw about 600 ml of plasma from a donor in about 45 minutes.

And yet another object of this invention is the provision of plasmapheresis apparatus/process for the withdrawal of plasma in which the operational strategy can easily by adapted according to the donor, the requirements of the operator and the characteristics of the membrane apparatus employed.

Briefly, the present invention features improved plasmapheresis apparatus comprising, and with reference to the attached Figures of Drawing:

(i) means 1 for withdrawing blood from a donor;

(ii) a membrane filtration cell 2 separating the blood into a fraction which has passed through the membrane and which consists of plasma, and into a fraction which has not passed through the membrane;

(iii) a first conduit 5 connecting the withdrawal means 1 to the inlet 6 of the upstream compartment 3 of the membrane filtration cell 2;

(iv) a pump 7 situated along said conduit 5;

(v) a pressure sensor 14 for the blood circulating in the conduit 5, said sensor being located between the pump 7 and the inlet 6 of the upstream compartment 3;

(vi) an inflatable tourniquet 21;

(vii) means enabling inflation or deflation of the tourniquet 21;

(viii) a second conduit 16 connecting the outlet 15 of the upstream compartment 3 of the membrane filtration cell 2 to a vessel 17 for collecting the fraction of the blood which has not been filtered through the membrane;

(ix) a pump 18 situated along the second conduit 16 and rotating in the same direction as the pump 7;

(x) a second pressure sensor 19 situated along the conduit 16 between the said pump 18 and the outlet 15 of the upstream compartment 3 of the membrane filtration cell 2;

(xi) a vessel 20 for collecting the plasma which has been filtered through the membrane, such vessel 20 being in communicating relationship with the outlet of the downstream compartment 4 of the membrane filtration cell 2;

(xii) means for measuring the volume of blood withdrawn from the donor during the withdrawal stage, at the beginning of which the tourniquet 21 is inflated or tightened about the limb of the donor;

(xiii) means for reversing the direction of rotation of the pumps 7 and 18 when the desired amount of blood has been withdrawn during the withdrawal stage, and thus ensuring the return of the blood from the vessel 17 to the donor, passing through the lines 16 and 5 and through the upstream compartment 3 of the membrane filtration cell 2, the tourniquet 21 being deflated upon commencement of the return stage; and (xiv) means 27 enabling monitoring or determining when the completion of the return stage has been reached, and ensuring that a return stage switches to a withdrawal stage.

The present invention also features a plasmapheresis technique utilizing the aforesaid apparatus.

BRIEF DESCRIPTION OF THE DRAWINGS

The description of the apparatus according to the present invention will be understood more clearly with reference to the attached Figures of Drawing, which illustrates, in a simplified manner, by way of non-limiting examples and with no fixed scale, particular embodiments of said apparatus.

DETAILED DESCRIPTION OF THE INVENTION

Figure 1:
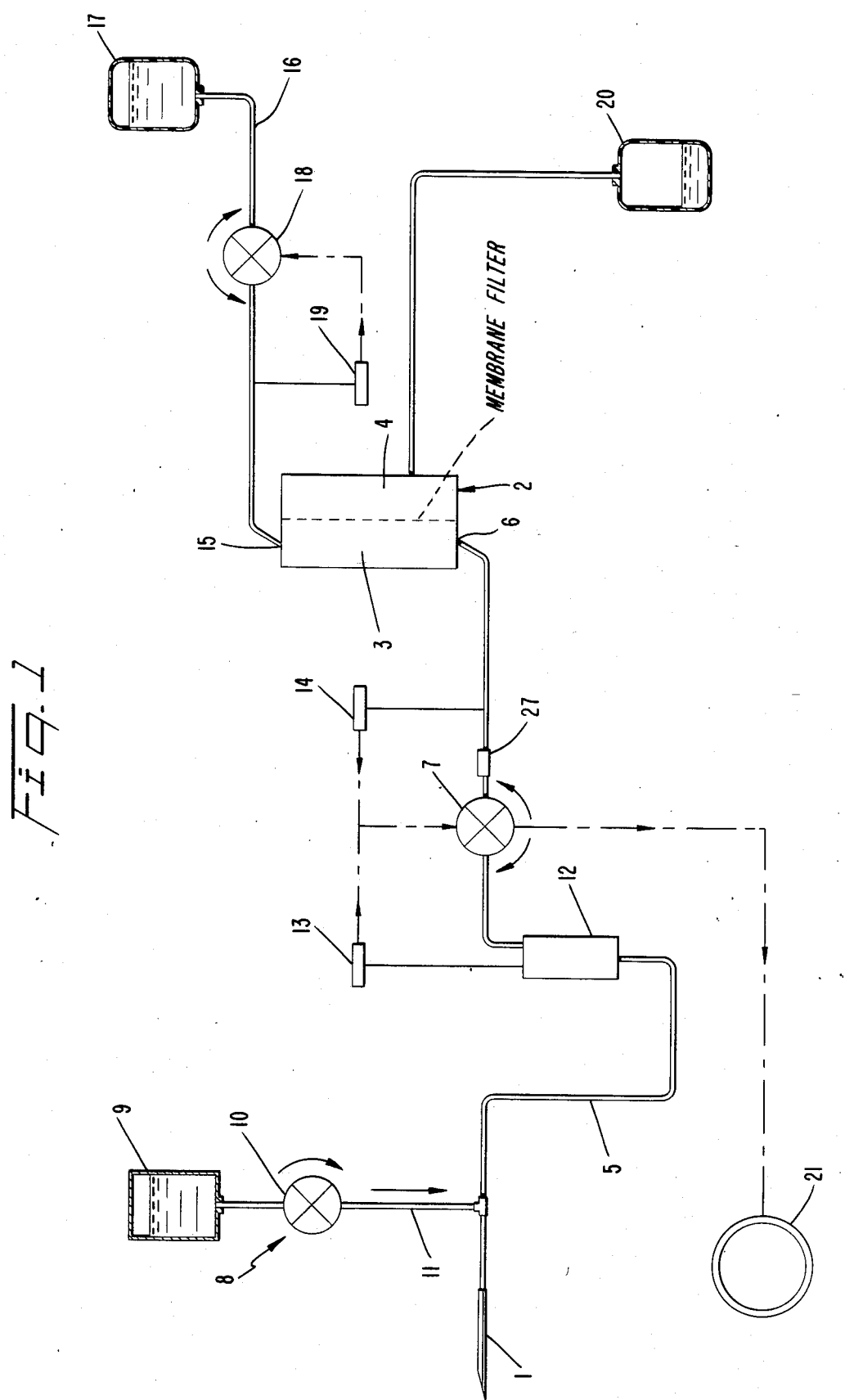
FIG. 1 is a schematic diagram of one embodiment of apparatus according to the present invention.

More particularly according to this invention, and with specific reference to FIG. 1, there is illustrated device for withdrawing blood from a donor patient comprising a needle 1 for the withdrawal of blood. By way of example, such needle can have an external diameter of 1.65 mm and an internal diameter of 1.45 mm, such as those typically employed in blood transfusion centers and conventially designated as 16 G needles. A membrane filtration cell 2, comprising an upstream compartment 3 and a downstream compartment 4, is operably connected to the needle 1 by a first conduit 5 extending from the needle 1 to the inlet 6 of the upstream compartment 3 of the membrane cell. This conduit 5 typically comprises a plastic tube, for example, made of polyvinyl chloride. Along this conduit 5, there is situated a pump 7 capable of rotating in either direction, which is advantageously of the peristaltic pump type. Such pumps are marketed, for example, by Hospal under the trademark RP 01. Between the pump 7 and the needle 1, there is a device 8 for injecting an anticoagulant into the blood emanating from the donor, for example, a glucose solution containing 35.6 g/liter of trisodium citrate, marketed as AB 16 from Bieluz. This device 8 comprises, for example, a reservoir 9 of anticoagulant, a conduit 11 operably connected to the conduit 5 and to the reservoir 9, and a pump 10, for example, of peristaltic type, situated along the conduit 11. This conduit 11 is connected to the conduit 5 as close as possible to the needle 1. A bubble detector 12 and a pressure sensor 13 operably communicate with the conduit 5 between the point of connection of the conduits 11 and 5 and the pump 7. A pressure detector 14 is also arranged between the pump 7 and the inlet 6 of the upstream compartment 3 of the membrane filtration cell 2. The outlet 15 of the upstream compartment 3 of the membrane filtration cell 2 is connected by a conduit 16 to a vessel 17 for collecting the fraction of the blood which has come into contact with the membrane separator without passing therethrough. This conduit 16 can be made of the same material and can have the same diameters as the conduit 5, while the vessel 17 is advantageously comprised of a flexible plastic bag. A pump 18 is situated along the conduit 16 and can rotate in either direction, this pump advantageously also being of peristaltic type. Between the outlet 16 of the upstream compartment 3 of the membrane filtration cell 2 and the pump 18, there is located a pressure sensor 19 along the conduit 16. The downstream compartment 4 of the separator is connected to a vessel 20 for collecting the plasma which has passed through the membrane, this vessel 20 being, for example, a plastic bag, the interior of which is in communication with atmospheric pressure, for example, via a sterile plug located at its upper end. This vessel 20 can also be a flexible plastic bag such as those marketed by Fenwal as "transfer-pack" R-2022.

The membrane, per se, comprising the filtration cell 2 referred to above can be in planar form, in spiral form or in the form of small thin tubes such as hollow fibers. If the membrane comprises a plurality of hollow fibers, the blood advantageously circulates inside the hollow fibers, the internal portions of the fibers together defining the upstream compartment 3 of the separator. If the membrane is in the planar or spiral form, the blood advantageously circulates between two membranes or groups of two membranes defining the upstream compartment 3 of the separator 2.

The membranes employed are preferably those which make it possible to collect a plasma in which all of the proteins in the initial blood are found again in the same proportions, in which the protein concentration is more than 55.5 g/liter, in which there are no red corpuscles and in which the platelet concentration is less than 15,000 platelets per $mm^3$. The membranes selected are those which also make it possible to avoid haemolysis of the blood circulating in contact with same, while at the same time permitting good filtration efficiencies.

These membranes advantageously have a latex rejection level of less than 75% for particles of a size of 0.27 micron and they have a latex rejection level of more than 15% for particles of a size of 0.64 micron. Preferably, the rejection level for particles of a size of 0.27 micron is less than 30% and the rejection level for latex particles of a size of 0.64 micron is more than 90%.

If the membranes are planar, this measurement of the latex rejection level is carried out by the following procedure:

50 ml of a suspension of sized polystyrene particles having a diameter of 0.27–0.4 or 0.64 micron (marketed by Rhone-Poulenc under the trademark Estapor), diluted to 0.1% strength with distilled water treated with 1% of a surface-active agent (an alkylarylsulfonate marketed as SINOZON NAS 60 by Sinnova), are introduced into a cell of the type Amicon Model 52.

The Amicon cell is fitted with a sample of membrane strengthened by a web. An air pressure corresponding to 20 cm of water is established. The first six milliliters of filtrate are recovered and the concentration (cf) of sized particles therein is determined.

The rejection level is determined according to the formula:

$$\frac{(0.1 - cf) \times 100}{0.1}$$

Membranes having the above characteristics are typically fabricated from a synthetic polymer, for example, of cellulose esters (cellulose nitrate or the like), regenerated cellulose, polycarbonate or the like. These membranes can also be based on polyether-urethanes comprising heparin-modified ammonium groups, or can be made from an acrylonitrile copolymer. Advantageously, these membranes are strengthened by a web if they are in the form of planar membranes and have a thickness ranging from 50 to 200 microns.

The apparatus depicted in FIG. 1 also comprises an inflatable tourniquet 21 of a type which is in itself known, it being possible for this tourniquet to be inflated, if desired, by a device (which is also in itself known) comprising an electrovalve connected to a cylinder of pressurized gas, for example, nitrogen or freon. In FIG. 1, the dashed lines including arrows, between the pressure sensors 13, 14 and 19 and the pumps 7 and 18, indicate that the said sensors act on the pump in accordance with the set values which they have been given beforehand. Thus, the operation of the pumps is controlled by the set values of the sensors. The same applies to the tourniquet 21, the inflation (or deflation) of which is controlled by the direction of rotation of the pump 7.

Figure 2:
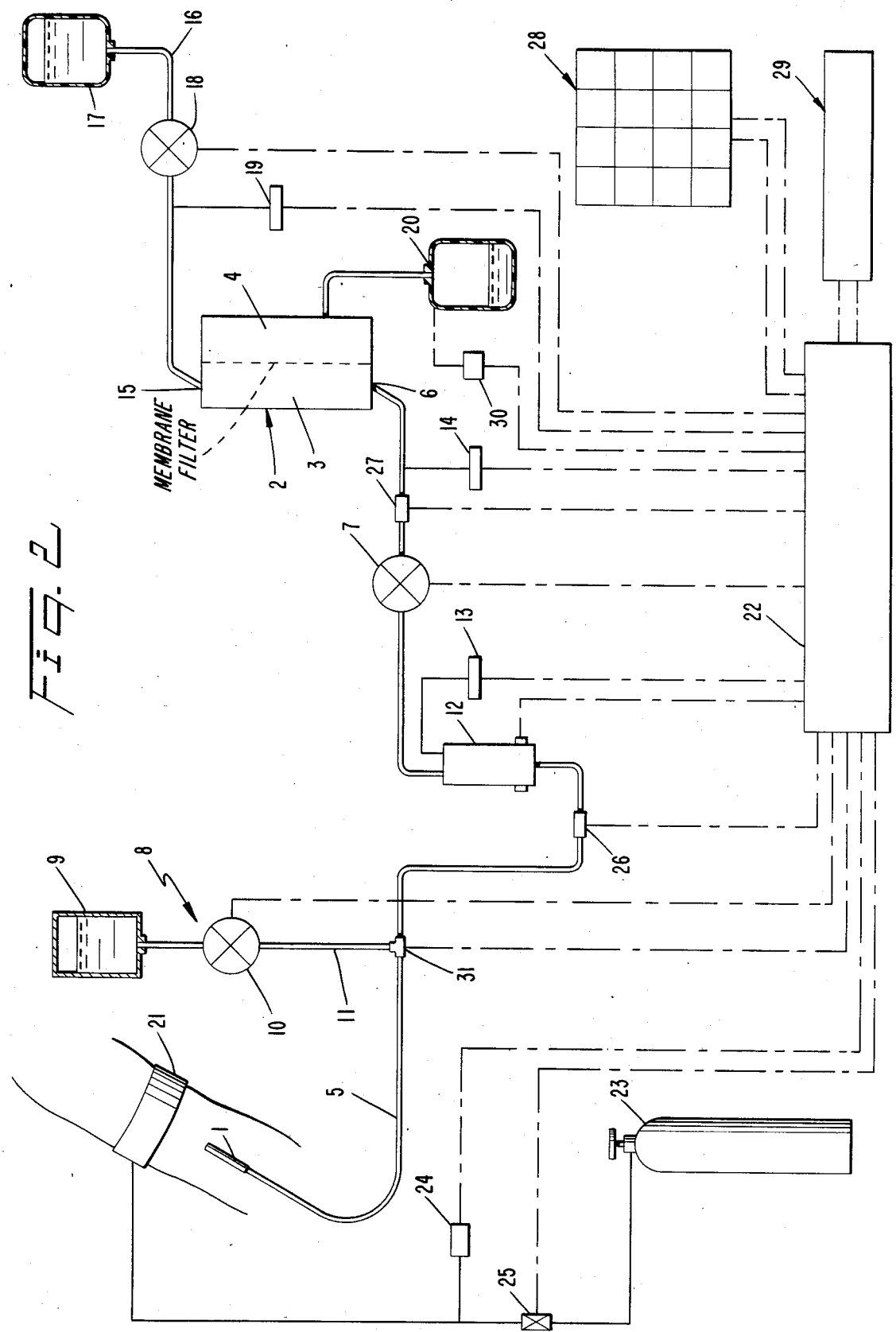
FIG. 2 is a schematic diagram of one embodiment of apparatus according to the invention, illustrating, in particular, the operative connections to a monitoring and control device.

In FIG. 2 apparatus is shown which is equivalent to that of FIG. 1, but including the electrical connections from the various elements to a logic unit 22 for control and monitoring, the electric leads being shown in dashed lines and the unit 22 being operably associated with a current supply (not shown).

The apparatus described above is used in the following manner. Initially, the conduit 11 is filled with citrate solution and, as the junction between the conduit 11 and the conduit 5 is in fact very close to the needle 1, it can be considered that the needle 1 is at least partially filled with this citrate solution. With the tourniquet inflated beforehand to the desired pressure (about 60 mm of mercury) using the cylinder 23 and the contact manometer 24, by opening the electrovalve 25 (these latter two elements being connected to the logic unit 22), the needle 1 is inserted into one of the donor's veins once the intended point of injection, which is located between the tourniquet and the end of the limb, has been sterilely prepared in conventional fashion. At this moment, the pump 10 injects citrate into the conduit 5, and the two pumps 7 and 18 rotate in the same direction and cause the blood to flow from the donor to the vessel 17, flowing through the upstream compartments 3 of the membrane filtration cell 2, where a portion of the plasma passes through the membrane separator and into the downstream compartment 4 connected to the bag 20. The pressure sensor 13 controls the pump 7 such that the pressure measured at this point along the conduit 5 always remains above a certain value, which is generally close to 0 mm of mercury and is designated the threshold pressure, in order to ensure that the pump 7 does not "draw" the blood directly from the donor's vein. If the pressure in this section of the conduit becomes less than the set value given to the sensor 13, the logic unit 22 acts automatically and momentarily stops or slows down the rotation of the pump 7 for as long as the desired pressure is not restored. The pressure sensor 14 is adjusted such that a pressure at the inlet 6 of the upstream compartment 3 which is greater than a maximum value, for example, a relative value ranging from 40 to 100 mm of mercury, preferably ranging from 60 to 90 mm of mercury, is automatically detected. If this desired maximum value is exceeded, the logic unit 22 automatically stops the pump 7. The sensor 19 makes it possible to ensure a relative pressure value ranging from 0 to 20 mm of mercury at the outlet 15 of the upstream compartment 3 of the separator 2, while the downstream compartment 4 is at atmospheric pressure. If the pressure at the outlet 15 of the upstream compartment 3 exceeds the desired maximum pressure, the logic unit 22 for control and monitoring automatically acts on the pump 18 to accelerate the rotation of its motor, namely, to increase its throughput.

The period during which the blood is exiting the donor's vein is called the withdrawal stage. This stage is terminated, for example, according to the predetermined volume of blood which it is desired to withdraw from the donor, this volume of course always being less than the volume of the vessel 17 for collecting the blood. Advantageously, a tachometric device is connected to the pump 7 and, when the desired volume of blood has been withdrawn from the donor, the logic unit 22 acts and stops the pumps 7, 10 and 18. The logic unit then acts simultaneously on the electrovalve 25, which takes up a position such that the tourniquet 21 deflates, and it causes the pumps 7 and 18 to rotate in the opposite direction to that of the preceding so-called withdrawal stage. The so-called "return of the blood to the donor" stage then starts and, during this stage, the blood contained in the bag 17 again passes through the upstream compartment 3 of the membrane filtration cell 2. In the course of the return stage, during which the citrate pump 11 is at rest, the sensor 19 performs a safety function and is adjusted such that the relative pressure does not exceed a certain value fixed in advance, for example, ranging from 40 to 100 mm of mercury, preferably ranging from 60 to 90 mm of mercury, when the blood enters the compartment 3 of the membrane separator 2; the blood then enters the separator via the conduit 15 noted in FIGS. 1 and 2. If this predetermined pressure value is exceeded, the logic unit 22 acts on the pump 18 and stops it, at least momentarily. The sensor 14 ensures that the blood leaving the separator via the line 6 is at a relative pressure ranging from 0 to 20 mm of mercury, while the downstream compartment 4 of the separator is at atmospheric pressure. If the fixed value is exceeded, the logic unit 22 immediately acts to accelerate the rotation of the pump 7, namely, to increase its throughput. During the return stage, the blood emanating from the vessel or bag 17, and from which a fraction of the plasma has already been removed, is filtered again by passage in contact with the membrane, and an additional fraction of its plasma is removed and passes into the downstream compartment 4 of the separator 2 and then into the bag 20. The blood then passes through the bubble detector 12. If bubbles are detected by the bubble detector 12, the logic unit 22 immediately stops the pumps 7 and 18 and, if necessary, acts on a clamp 26, or blocking device, which closes the conduit 5. During the return stage, the pressure sensor 13 performs a safety function in the sense that it is adjusted such that the pressure of the blood does not exceed a certain predetermined value. If this value is exceeded, for example, as a result of obstruction of the needle 1, the logic unit 22 immediately intervenes to stop the pump 7. During the return stage, the blood may pass through a conventional filter provided in the bubble detector 12, in order to prevent undesirable particles from being returned to the donor. This filter can, for example, move aside during the withdrawal stage, and it falls back onto a seat, provided in the bubble detector, during the return stage. The completion of the return stage is detected, for example, by an optical detector 27 provided along the conduit 5. When no more blood (from which a portion of the plasma has been removed) is passing through at the point where the detector 27 is located, the logic unit 22 intervenes to stop the return stage and to cause the equipment to revert to a withdrawal stage. Thus, the pumps 7 and 18 are stopped and are re-started such that they both rotate in the same direction, but in the opposite direction to that of the return stage, while the tourniquet 21 is inflated and the citrate pump 10 is activated. When, upon completion of a return stage, it is seen that the plasma bag 20 contains a sufficient amount of plasma, the operation is stopped completely.

In general, the throughput of the pump 10 is adjusted such that, during the so-called withdrawal stage, there is one volume of citrate per 8 volumes of blood, or preferably 1 volume of citrate per 16 volumes of blood, the ratio being selected by the user. This dilution ratio is advantageously obtained by bringing the speed of rotation of the pump 10 under the control of the speed of rotation of the pump 7.

It is readily apparent that a very high level of automation can be imparted to the apparatus according to the present invention. Thus, as is shown more paricularly in FIG. 2, the logic unit 22 for control and monitoring can be connected to a keyboard 28 and a display unit 29. Likewise, the logic unit 22 can be connected to a synoptic table (not shown), on which the location of any anomaly is indicated to the operator by a signal lamp, for example, at the same time as a sound signal is actuated. On the keyboard 28, it is possible to select the volume of blood which it is desired to circulate during the withdrawal stage (for example, 300, 350, 400, 450 cm$^3$ of blood) by pressing the corresponding key. It is also possible to select the volume of plasma which it is desired to withdraw during the session (for example, 400, 500 or 600 cm$^3$) by pressing the corresponding key. Thus, a device 30 is advantageously provided on the plasma bag 20 such as to give an instantaneous measurement of the volume (or the weight) of plasma withdrawn during a particular session, this device 30, which is in itself known, being connected to the logic unit 22. A key for the automatic actuation of the conduit 11, before the donor is injected, can also be provided on the keyboard 28. By pressing this key, the pump 10 starts, and it stops automatically when the citrate solution is detected, for example, at the junction 31 between the two conduits 11 and 5. The keyboard 28 can also be provided, for example, with a key for indicating, on the display unit 29, a measurement of the instantaneous volume of plasma in the bag 20 at any time, a key for indicating, on the display unit 29, a measurement of the flow of blood from the pump 7, a key for indicating a measurement of the time for which the present session has been running, and so on. The apparatus can comprise, linked to the logic unit 22 and the values displayed on the keyboard 28 concerning the volume of blood desired during the withdrawal stage and the total volume of plasma desired, an integrating system acting during the last withdrawal stage, such that the withdrawal volume makes it possible to obtain the desired total volume of plasma upon completion of the last return stage.

Numerous variations of the apparatus described above will be apparent to those skilled in the art. By way of example, the apparatus can include a collapsible balloon along the conduit 5 between the junction 31 and the clamp 26. This balloon then performs a dual safety function with the pressure sensor 13 in the sense that it blocks itself when the throughput of the pump 7 is greater than that of the vein, if the sensor has not functioned during the withdrawal stage. If appropriate, this collapsible balloon can be substituted for the sensor 13.

Likewise, the device 8 for injecting the anticoagulant may be omitted insofar as the interior of the needle 1, of the bubble detector 12 and of the conduits 5 and 16 is covered, for example, with a polymer based on polyether-urethanes containing heparin-modified ammonium groups, such as those described, in particular, in U.S. Pat. No. 4,046,725. If appropriate, the conduits 5 and 16 can be made of a polymer such as those described in the abovementioned U.S. patent, or of a mixture of polyvinyl chloride and a polyether-urethane containing heparin-modified ammonium groups, such as those mixtures referred to in published European patent application No. 12,701. The microporous membrane can also be prepared from a mixture of polymers according to European patent application No. 12,701.

Utilizing the apparatus such as shown in FIGS. 1 and 2 and described above, plasmapheresis operations have been carried out on a donor using, by way of example, a membrane filtration cell 2 having a total membrane surface area of 600 cm$^2$ and comprising two microporous membranes arranged face-to-face (forming the upstream compartment 3), between which the blood circulates. The membranes each have a length of 30 cm and a width of 10 cm and are strengthened by a web, as described more clearly below. The average thickness of the film of blood is 370 microns. The withdrawal device 1 is a needle having an external diameter of 1.65 mm and an internal diameter of 1.45 mm. The conduits 5 and 6 are made of polyvinyl chloride (PVC) and have an internal diameter of 3.5 mm. The conduit 11 is made of PVC and has an internal diameter of 0.9 mm. The pump 10 is a peristaltic pump (reference RP 04, marketed by Hospal), the said pump having a pump casing made of silicone.

The pumps 7 and 18 are peristaltic pumps (reference RP 01, marketed by Hospal), the said pumps having a pump casing made of silicone. The vessels 17 and 18 have a capacity of 1,000 cm³ and are made of PVC.

The sensor 13 is a sensor marketed by National Semiconductor under the trademark LX 1801 GB, of which the displayed pressure is set at 10 mm of mercury during the withdrawal stage and of which the maximum pressure value is set at 100 mm of mercury during the return stage. The sensors 14 and 19 are sensors marketed under the same trademark and the same reference as the sensor 13. The sensor 14 is set at a maximum relative pressure of 80 mm of mercury for the withdrawal stage and at a minimum relative pressure of 10 mm of mercury during the return stage, while the sensor 19 is set at a relative pressure of 10 mm of mercury for the withdrawal stage and at a relative pressure of 80 mm of mercury for the return stage. Thus, the pressure of the blood in circulation is greater than the pressure of the plasma collected in the downstream compartment 4 of the membrane cell, which is at atmospheric pressure. The average trans-membrane pressure is equal to $$\frac{80 + 10}{2} = 45 \text{ mm}$$

of mercury.

During each withdrawal stage, the tourniquet is inflated to 60 mm of mercury and the flow of the citratetreated blood at the inlet of the separator is 85 ml/minute on average.

The membrane employed is a woven membrane obtained from a solution of polymer in an organic solvent, which is poured over a web rotating in contact with a strip having a very smooth surface. This solution comprises 8% by weight, in an N-methylpyrrolidone/glycerol mixture (70.8/21.2%), of an acrylonitrile/methyl methacrylate/sodium methallylsulfonate copolymer comprising 7.75% by weight of methyl methacrylate and 80 milliequivalents/kg of acid sites. This polymer has a specific viscosity of 0.3 at 20° C. in a dimethylformamide solution containing 2 g/liter.

The web used is a single-filament fabric made of polyethyleneglycol terephthalate, of which the mesh size is 75 microns, the filament diameter is 55 microns and the proportion of voids is 33%. The weight of this web is 55 g/m².

The microporous woven membrane obtained has a thickness of 120 microns and its weight is 10 g of polymer per m² of dry membrane. The microstructure of the polymer phase of the membrane is spongy and uniform. Its porosity is 80%, the porosity being defined as the ratio (multiplied by 100) of the volume of the pores to the total volume of the membrane (polymer+pores).

The flow of water (treated with 1% of a surfaceactive agent) through this woven membrane is 4.5 ml/hour. cm². mm Hg. The latex rejection level of this membrane is:

(a) 5% to 15% for a latex having a particle size of 0.27 micron;

(b) 65% to 80% for a latex having a particle size of 0.4 micron; and (c) 98% to 100% for a latex having a particle size of 0.64 micron.

Using the apparatus described above, and fixing a blood volume of 350 cm³ during the withdrawal stage, a total of volume of 600 cm³ of plasma to be collected, and a ratio of volume of anticoagulant solution/volume of blood of 1/16, during each withdrawal stage, the plasmapheresis operation was completed in 44 minutes after having carried out 6 withdrawal stages and 6 return stages.

The plasma collected is virtually non-cellular. It contains no contamination by red corpuscles and contains only 3,000 platelets per mm³. The protein concentration of the plasma is 57 g/liter.

The apparatus described above can quite obviously be used on animals (dogs, horses and the like), in particular for plasmapheresis operations.

In general, this apparatus can be used whenever it is desired to inject a subject (human or aminal) at only one point, with a simple needle (having only one internal channel), the liquid withdrawn from the subject, which is generally blood, being circulated firstly in one direction (withdrawal stage) and then in the opposite direction (return stage), in contact with a microporous membrane comprising a membrane filtration cell, there being means for controlling the desired pressures at which the blood enters and leaves the membrane cell during the two stages. Thus, with this apparatus, it is possible to remove elements from the blood in circulation, a first time during the withdrawal stage and a second time during the return stage, when the fraction of the blood which has not passed through the membrane is returned to the patent. Thus, the apparatus described above can be used for applications other than plasmapheresis. According to the separation characteristics (such as, for example, the level of rejection of sized latex particles) of the membranes used, it will thus be possible, for example, to remove only a portion of the proteins or only a portion of the other constituent elements of the plasma from the blood in circulation. It is thus also possible, with the apparatus described above, to perform haemofiltration sessions, for example, by means of re-injection with a substitute liquid, this re-injection being controlled by the amount of filtered liquid collected in the vessel 20.

The subject apparatus can also be used for plasmatic exchange operations, namely, by re-injecting a patient with a plasma in an amount equivalent to that which has been withdrawn from said patient, by means of a pump (not shown) and a conduit (not shown) connected, for example, to the conduit 5 between the inlet 6 of the separator and the sensor 14, the said pump operating during each return stage. The subject apparatus can also be used in peritoneal dialysis, in which case the tourniquet is no longer necessary.

To be suitable for all of the possible uses noted above, the subject apparatus can of course include variants as regards certain of its structural elements. By way of example, the pump 18, although used preferentially, may be replaced by equivalent means performing the same functions, namely, in particular, ensuring a certain maximum desired pressure during the return stage.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. Apparatus for the withdrawal, fractionation and return of liquid materials from and to a donor source, comprising:

(i) means for withdrawing a liquid material from a donor source;

(ii) a membraneous filtration cell which comprises (1) a membrane separator, (2) a cell compartment downstream therefrom for enclosing that fraction of said liquid material which is filtered through said membrane separator and (3) a cell compartment upstream thereof for enclosing that fraction of said liquid material which is not filtered through said membrane separator;

(iii) conduit means establishing communicating relationship between said withdrawal means (i) and the inlet end of said upstream cell compartment (ii) (3), having reversible liquid material pumping means (x) operably engaged along said conduit means (iii) and pressure sensor means (xi) for the pressure of liquid material circulating in each conduit means (iii), said pressure sensor means being operably engaged along said conduit means (iii), between said pumping means (x) and the inlet end of said upstream cell compartment (ii)(3);

(iv) a collection vessel downstream from the outlet end of said upstream cell compartment (ii)(3) for that fraction of liquid material which is not filtered through the membrane separator;

(v) conduit means establishing communicating relationship between the outlet end of said upstream cell compartment (ii)(3) and said collection vessel (iv);

(iv) means for determining the volume of liquid material withdrawn from the donor source during a withdrawal stage;

(vii) means for returning the unfiltered liquid material fraction from said collection vessel (iv) to said donor source through said compartment (ii) (3) of said filtration cell upon predetermined completion of said withdrawal stage, by recycling same back to said donor source through said conduit means (v), said upstream cell compartment (ii) (3) and said conduit means (iii);

(viii) a collection vessel downstream from the outlet end of said downstream cell compartment (ii) (2) for that fraction of liquid material which is filtered through the membrane separator, and conduit means (ix) establishing communicating relationship between the outlet end of said downstream cell compartment (ii) (2) and said collection vessel (viii); and (xiii) means for ensuring desired pressures at the outlet end of said upstream cell compartment (ii) (3) upon withdrawal of liquid material from the donor source and at the inlet end of said upstream cell compartment (ii) (3) upon return of the unfiltered fraction of liquid material from the collection vessel (iv) to the donor source.

2. The apparatus as defined by claim 1, further comprising second pressure sensor means (xii) operably engaged along said conduit means (v), between said collection vessel (iv) and the outlet end of said upstream compartment (ii) (3).

3. The apparatus as defined by claim 2, wherein said means (xiii) is responsive to said second pressure sensor means (xii).

4. The apparatus as defined by claim 3, further comprising means (xiv) for detecting completion of predetermined return stage, and for switching mode thereof to a withdrawal stage.

5. The apparatus as defined by claim 4, wherein said means (xiii) comprises pumping means adapted to operate in the same direction, and at the same time, as the pumping means (x).

6. The apparatus as defined by claim 4, comprising plasmapheresis apparatus wherein the donor source is a living mammal, the liquid material is blood, and the means (i) is a single blood withdrawal needle.

7. The plasmapheresis apparatus as defined by claim 6, further comprising an inflatable tourniquet (xvi) for a limb of said living mammal, and means (xvii) for both inflating said tourniquet about said limb during a blood withdrawal stage and deflating same during a blood fraction return stage.

8. The plasmapheresis apparatus as defined by claim 7, said means (xvii) being adopted to inflate said tourniquet upon commencement of a blood withdrawal stage and to deflate said tourniquet upon commencement of a blood fraction return stage.

9. The plasmapheresis apparatus as defined by claim 8, said means (xvii) for inflating and deflating said tourniquet (xvi) comprising a pressurized gas reservoir (xviii), an electrovalve (xix) and a contact monometer (xx), with the opening of said valve (xix) being controlled by the direction of operation of the pumping means (x).

10. The plasmapheresis apparatus as defined by claim 9, further comprising a blood bubble detector (xxi) and third pressure sensor means (xxii) operably engaged along said conduit means (iii), between said blood withdrawal needle (i) and said pumping means (x).

11. The plasmapheresis apparatus as defined by claim 9, further comprising means (xxiii) for introducing an anticoagulant into blood being withdrawn into the conduit means (iii), in close proximity to said blood withdrawal needle (i).

12. The plasmapheresis apparatus as defined by claim 9, said pumping means (x) being responsive to said pressure sensor means (xi), and said pumping means (xiii) being responsive to said second pressure sensor means (xii).

13. The plasmapheresis apparatus as defined by claim 12, said pressure sensor means (xi) being adopted to ensure a maximum relative pressure ranging from 40 to 100 mm Hg of the blood inleting said filtration cell (ii), during a withdrawal stage thereof, and to ensure a relative blood pressure of less than 20 mm Hg during a return stage thereof, and said pressure sensor means (xii) being adopted to ensure a relative blood pressure of less than 20 mm Hg at the outlet end of said upstream compartment (ii) (3) during a blood withdrawal stage, and to ensure a maximum relative blood pressure ranging from 40 to 100 mm Hg during a return stage thereof, with said downstream compartment (ii) (23) being at atmospheric pressure.

14. The plasmapheresis apparatus as defined by claim 13, said pumping means (x) also being responsive to said third pressure sensor means (xxii) and being adopted to ensure that the pressure of the blood within said conduit means (iii) between said blood withdrawal needle (i) and said pumping means (x) does not decrease below a predetermined minimum relative or threshold pressure during a blood withdrawal stage, as well as to ensure that the relative blood pressure does not exceed a predetermined maximum value during a blood return stage.

15. The plasmapheresis apparatus as defined by claim 14, further comprising means (xxiv) for determining at any time the amount of blood plasma in said collection vessel (viii).

16. The plasmapheresis apparatus as defined by claim 14, further comprising logic circuitry means (xxv) for the automatic monitoring and control of said blood withdrawal from, and blood return to, said living mammal.

17. The plasmapheresis apparatus as defined by claim 16, said logic circuitry means (xxv) comprising a keyboard (xxvi) adopted for predetermined selection of the total amount of blood desired to be withdrawn and the total amount of plasma desired to be collected, and said logic circuitry means (xxv) also being adopted to limit the volume of blood in final withdrawal stage circulation and to ensure that said total amount of plasma desired is collected upon completion of said final withdrawal stage.

18. The plasmapheresis apparatus as defined by claim 13, said membrane separator (ii) (1) having a latex rejection level of less than 75% for particles of a size of 0.27 micron, and a latex rejection level of more than 15% for particles of a size of 0.64 micron.

19. The plasmapheresis apparatus as defined by claim 18, said membrane separator (ii) (1) having a latex rejection level of less than 30% for particles of a size of 0.27 micron, and a latex rejection level of more than 90% for particles of a size of 0.64 micron.

20. The plasmapheresis apparatus as defined by claim 18, said membrane separator (ii) (1) being planar and web reinforced.

21. The plasmapheresis apparatus as defined by claim 20, said reinforcing web comprising single-filament polyester fabric.

22. The plasmapheresis apparatus as defined by claim 20, said reinforcing web comprising a fabric having a mesh opening size of about 75 microns and comprising about 55 micron filaments.

23. The plasmapheresis apparatus as defined by claim 20, said reinforcing web being woven and said separator having a thickness ranging from about 50 to 200 microns.

24. The plasmapheresis apparatus as defined by claim 18, said membrane separator (ii) (1) comprising a copolymer of acrylonitrile, methyl methacrylate and sodium methallylsulfonate.

25. The plasmapheresis apparatus as defined by claim 24, said copolymer comprising about 7.75% by weight of methacrylate and about 80 milliequivalents/kg of acid sites.

26. A plasmapheresis process, comprising withdrawing whole blood from a limb of a mammalian donor; pumping said whole blood into and through a membranous filtration cell which comprises a membrane separator and upstream and downstream blood fraction enclosing compartments on either side thereof, to separate said whole blood into two fractions by intimate contact thereof with said membrane separator, a first fraction which is unfiltered and which is pumped through said upstream compartment into an unfiltered blood fraction collection vessel, and a second plasma fraction which is filtered through said membrane separator into said downstream compartment and is thence passed into a blood plasma collection vessel; next terminating said whole blood withdrawal when the amount withdrawn has reached predetermined level; and then returning said first fraction from said unfiltered blood fraction collection vessel to said mammalian donor by pumping said first fraction from said unfiltered blood fraction collection vessel back through the upstream compartment of said membranous filtration cell and then to said mammalian donor, whereby said first blood fraction is placed in intimate contact with said membrane separator at least twice before being returned to said mammalian donor.

27. The plasmapheresis process as defined by claim 26, further comprising terminating said return cycle when essentially all of said first fraction from said unfiltered blood fraction collection vessel has been returned to said mammalian donor, and thence again commencing said withdrawal cycle.

28. The plasmapheresis process as defined by claim 27, comprising alternating said withdrawal and return cycles until a predetermined total amount of blood plasma has been collected.

29. The plasmapheresis process as defined by claim 28, said predetermined total amount of blood plasma having been collected upon completion of a return cycle.

30. The plasmapheresis process as defined by claim 28, an inflated tourniquet compressing the limb of the mammalian donor during each withdrawal cycle, and said tourniquet being deflated during each return cycle.

31. The plasmapheresis process as defined by claim 28, further comprising maintaining the relative pressure at which the blood being withdrawn enters the upstream compartment of the membranous filtration cell at no more than a predetermined maximum value (1), maintaining the relative pressure at which the blood fraction being withdrawn exits said upstream compartment at less than a predetermined maximum value (2), maintaining the relative pressure at which the blood fraction being returned enters said upstream compartment at no more than a predetermined maximum value (3), and maintaining the relative pressure at which the blood fraction being returned exits said upstream compartment at less than a predetermined maximum value (4).

32. The plasmapheresis process as defined by claim 31, said predetermined maximum pressures (1) and (3) ranging from 40 to 100 mm Hg, and said predetermined maximum pressures (2) and (4) being less than about 20 mm Hg.

33. The plasmapheresis process as defined by claim 32, said blood plasma collection vessel being at about atmospheric pressure.

34. The plasmapheresis process as defined by claim 33, said predetermined maximum pressures (1), (2), (3) and (4) being maintained by means of a plurality of pressure sensors and a plurality of pumping means responsive thereto.

35. The plasmapheresis process as defined by claim 32, comprising introducing an anticoagulant into said blood being withdrawn, at a point in close proximity to the point of blood withdrawal.

36. The plasmapheresis process as defined by claim 32, the blood and blood fraction respectively being withdrawn from and returned to said limb of the mammalian donor being via a single blood transfusion injection needle.

37. The plasmapheresis process as defined by claim 36, the same being wholly monitored and controlled by means comprising logic circuitry.

* * * * *